United States Patent [19]

VandenBerg

[11] Patent Number: Plant 7,389

[45] Date of Patent: Dec. 4, 1990

[54] CHRYSANTHEMUM PLANT NAMED BRONZE CAVALCADE

[75] Inventor: Cornelis P. VandenBerg, Salinas, Calif.

[73] Assignee: Yoder Brothers, Inc., Barberton, Ohio

[21] Appl. No.: 355,182

[22] Filed: May 22, 1989

[51] Int. Cl.[5] ..... A01H 5/00

[52] U.S. Cl. ..... Plt./79

[58] Field of Search ..... 800/280; 47/58, DIG. 8; Plt./78, 79

[56] References Cited

U.S. PATENT DOCUMENTS

| | | | |
|---|---|---|---|
| P.P. 5,351 | 11/1984 | Duffett | Plt. 78 |
| P.P. 5,352 | 11/1984 | Duffett | Plt. 78 |
| P.P. 5,400 | 2/1985 | Duffett | Plt. 78 |
| P.P. 5,621 | 12/1985 | Duffett | Plt. 78 |
| P.P. 5,786 | 8/1986 | Duffett | Plt. 78 |
| P.P. 5,818 | 12/1986 | van der Knaap | Plt. 78 |
| P.P. 5,819 | 12/1986 | Duffett | Plt. 78 |
| P.P. 6,223 | 7/1988 | Hesse | Plt. 78 |
| 4,616,099 | 10/1986 | Sparkes | 800/200 |

OTHER PUBLICATIONS

Gosling, S. G., ed. 1979, The Chrysanthemum Manual of the National Chrysanthemum Society, Publ. by the National Chrysanthemum Society, London, England, pp. 329–336.

Searle, et al, 1968, Chrysanthemums the Year Round, Blandford Press, London, pp. 27–29.

Broertjes, C., "Mutation Breeding of Chrysanthemums", *Ephytica 15* (1966): 156–162 Association Euratom–Ital, Wageningen.

Chan, A. P., "Chrysanthemum and Rose Mutations Induced by X Rays", Reprinted from Proceedings of the American Society for Horticultural Science, vol. 88, 1966, Plant Research Institute, Research Branch, Canada Dept. of Agriculture, Ottawa, Canada, pp. 613–620.

Broertjes, C. and A. M. Van Harten, *Application of Mutation Breeding Methods in the Improvement of Vegetatively Propagated Crops*, "Chrysanthemum", Elsevier Scientific Publishing Company, Amsterdam–Oxford–New York 1978, pp. 162–175.

Broertjes, C., P. Koene and J. W. H. Van Veen, "A Mutant of a Mutant of a Mutant of a . .. Irradiation of Progressive Radiation–Induced Mutants in a Mutation–Breeding Programme with Chrysanthemum morifolium Ram.", *Euphytica* 29 (1980): 525–530.

Teynor, Tim M., Peter D. Ascher, R. E. Widmer and J. J. Luby, "Inheritance of Flower Color in *Dendranthema grandiflora*"Tzvelev. (*Chrysanthemum morifolium* Ramat.) Using Cultivars and Inbreds., I. Plastid Pigmentation, and II Vacuole Pigmentation *Euphytica* 42 (1989): 199–207 and 297–305, Kluwer Academic Publishers, Netherlands.

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Bronze Cavalcade particularly characterized by its incurved capitulum form, standard capitulum type, medium orange-bronze ray floret color, diameter across face of capitulum of up to 14 cm at maturity when grown as a single stem standard cut mum, uniform nine week photoperiodic flowering response to short days, and medium plant height when grown as a single stem cut mum.

3 Drawing Sheets

The present invention comprises a new and distinct cultivar of Chrysanthemum, botanically known as *Dendranthema grandiflora*, and referred to by the cultivar name Bronze Cavalcade.

Bronze Cavalcade, identified as 70-181E02, is a product of a mutation induction program which had the objective of creating new Chrysanthemum cultivars that would expand the color range of an existing cultivar while retaining all other traits.

Bronze Cavalcade was discovered and selected by Cornelis P. VandenBerg on Nov. 30, 1984 in a controlled breeding program in Salinas, Calif., as one flowering plant within a flowering block established as rooted cuttings from stock plants which had been exposed as unrooted cuttings to an X-ray source of 1800 rads. The irradiated parent was the cultivar Marmalade, disclosed in U.S. P.P. No. 5,281.

The first act of asexual reproduction of Bronze Cavalcade was accomplished when vegetative cuttings were taken from the initial selection in January of 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Bronze Cavalcade are firmly fixed and are retained through successive generations of asexual reproduction.

Bronze Cavalcade has not been observed under all possible environmental conditions. The phenotype may vary significantly with variations in environment such as temperature, light intensity and daylength.

The following observations, measurements and comparisons describe plants grown in Salinas, Calif., and Leamington, Canada, under greenhouse conditions which approximate those generally used in commercial greenhouse practice.

The following traits have been repeatedly observed and are determined to be basic characteristics of Bronze Cavalcade, which, in combination, distinguish this Chrysanthemum as a new and distinct cultivar:

1. Incurved capitulum form.
2. Standard capitulum type.
3. Medium orange-bronze ray floret color.
4. Diameter across face of capitulum up to 14 cm at maturity, when grown as a single stem standard cut mum.

5. Uniform nine week photoperiodic flowering respose to short days.

6. Medium plant height, requiring 14 long days prior to short days to attain a flowered plant height of 90 to 100 cm for year-round flowerings when grown as a single stem cut mum.

The accompanying photographic drawings show typical inflorescence and leaf characteristics of Bronze Cavalcade, with the colors being as nearly true as possible with illustrations of this type. Sheet 1 is a color photograph of Bronze Cavalcade grown as a standard cut mum. Sheet 2 is a black and white photograph of three views of the inflorescence of Bronze Cavalcade. Sheet 3 is a black and white photograph showing the upper and under sides of the leaves of Bronze Cavalcade at three stages of development (mature, intermediate and immature).

Of the commercial cultivars known to the inventor, the most similar in comparison to Bronze Cavalcade is the parent cultivar Marmalade. All traits of Bronze Cavalcade are similar of those of Marmalade, except the color of ray florets. The color or ray florets of Bronze Cavalcade is a medium orange-bronze, while Marmalade has a much lighter honey-bronze ray floret color.

In the following description color references are made to The Royal Horticultural Society Colour Chart. The exact color for the corolla of florets of Bronze Cavalcade is not represented in the R.H.S. Colour Chart, and the color values given are those closest to the actual color of Bronze Cavalcade. The color values are determined on plant material grown as a single stem standard cut mum in Salinas, Calif., on Sept. 1, 1988.

Classification:

*Botanical.*—*Dendranthema grandiflora* cv Bronze Cavalcade.

*Commercial.*—Incurved standard cut mum.

Inflorescence

A. Capitulum:
- *Form.*—Incurved.
- *Type.*—Standard.
- *Diameter across face.*—Up to 14 cm at maturity.

B. Corolla of ray florets:
- *Color (general tonality from a distance of three meters).*—Medium orange-bronze.
- *Color (upper surface).*—Between 163B-D and 20A.
- *Color (under surface).*—15B to 15C
- *Shape.*—Cross-section concave; longitudinal incurved.

C. Corolla of Disc Florets:
- *Color (mature).*—6D.
- *Color (immature).*—154B.

D. Reproductive Organs:
- *Androecium.*—Present on disc florets only, very few; scant pollen.
- *Gynoecium.*—Present on both ray and disc florets.

Plant

A. General Appearance:
- Height.—Medium; 90 to 100 cm as a single stem cut mum with 14 long days prior to short days.

B. Foliage:
- *Color (upper surface).*—147A.
- *Color (under surface).*—147B.
- *Shape.*—Lobed and serrated.

I claim:

1. A new and distinct Chrysanthemum plant named Bronze Cavalcade, as described and illustrated.

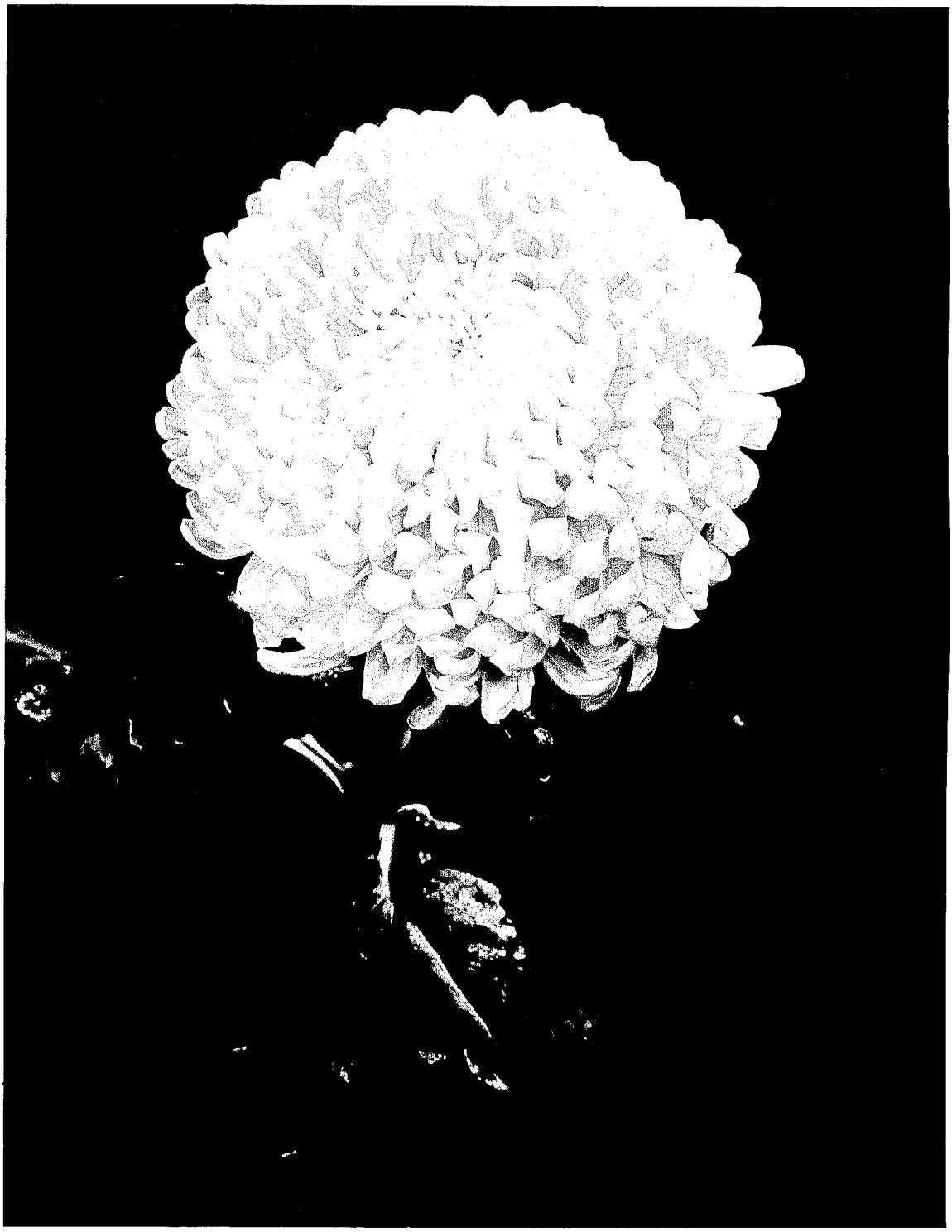

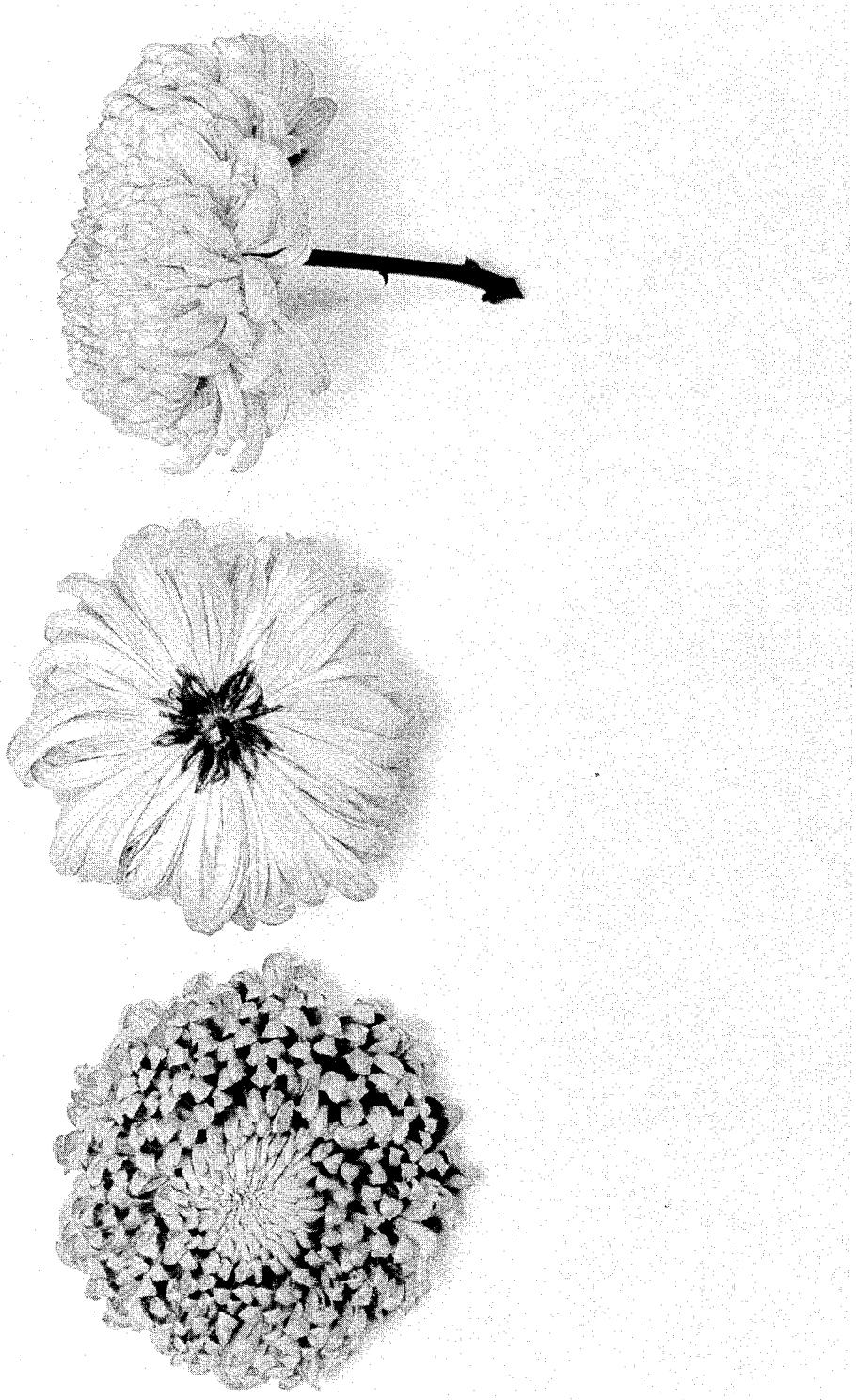

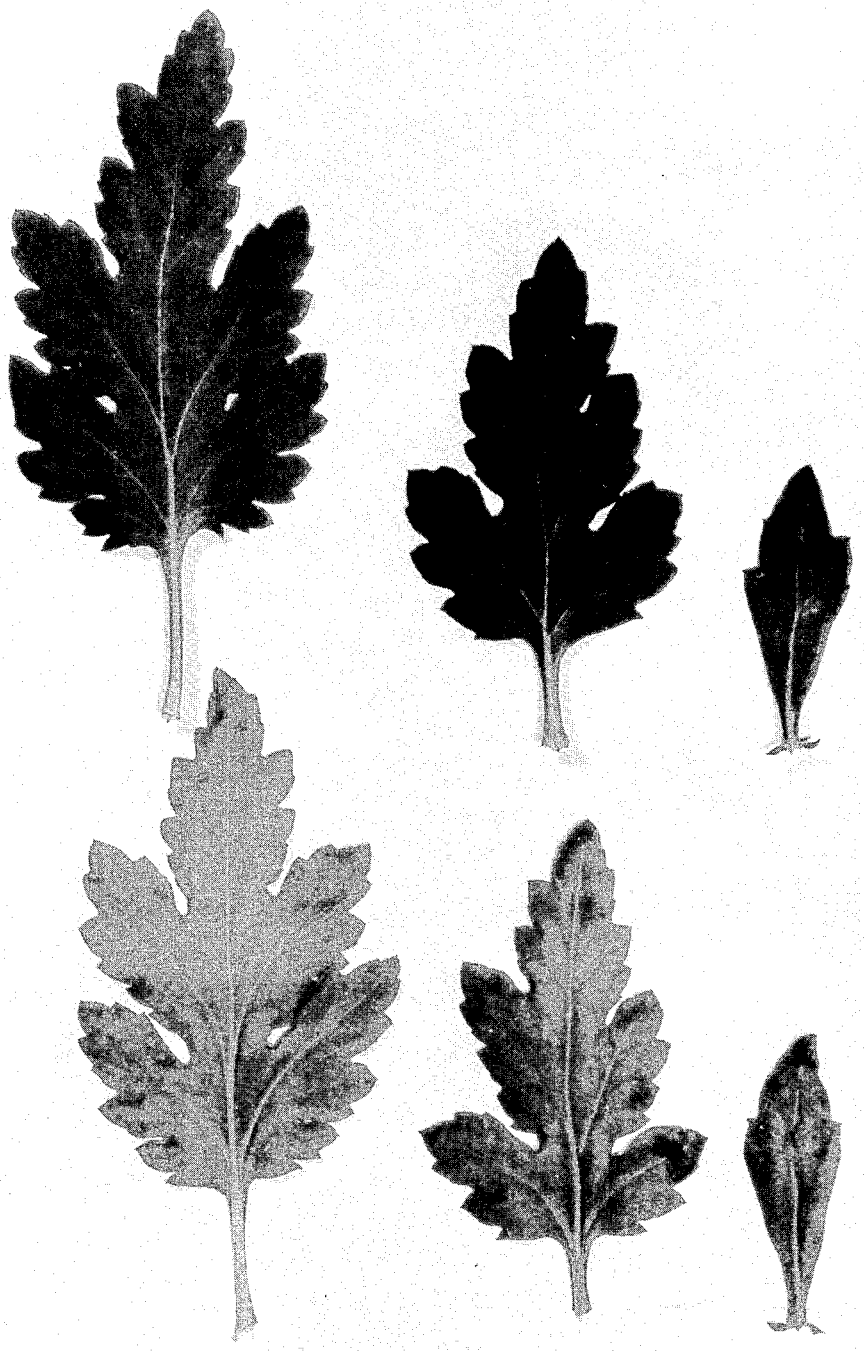

* * * * *